(12) United States Patent
Pryor et al.

(10) Patent No.: US 7,396,936 B1
(45) Date of Patent: Jul. 8, 2008

(54) MODULATORS OF CALCITONIN AND AMYLIN RECEPTOR ACTIVITY

(75) Inventors: Kent Pryor, San Diego, CA (US); Jan Urban, San Diego, CA (US); Lubomir Sebo, San Diego, CA (US); Stephen Miller, San Diego, CA (US); Nancy Delaet, San Diego, CA (US)

(73) Assignee: Kemia, Inc., San Diego, CA (US)

( * ) Notice: Subject to any disclaimer, the term of this patent is extended or adjusted under 35 U.S.C. 154(b) by 49 days.

(21) Appl. No.: 11/270,046

(22) Filed: Nov. 9, 2005

Related U.S. Application Data

(60) Provisional application No. 60/626,825, filed on Nov. 9, 2004.

(51) Int. Cl.
  C07D 405/02 (2006.01)
  C07D 401/02 (2006.01)
  A61K 31/44 (2006.01)
  A61K 31/465 (2006.01)

(52) U.S. Cl. .................. 546/283.4; 546/268.1; 514/336

(58) Field of Classification Search .............. 546/283.4, 546/268.1; 514/336, 355, 356, 340
  See application file for complete search history.

(56) References Cited

U.S. PATENT DOCUMENTS

| | | | |
|---|---|---|---|
| 4,985,242 A | 1/1991 | Sekine et al. | |
| 4,988,512 A | 1/1991 | Azria | |
| 4,992,417 A | 2/1991 | Katsoyannis et al. | |
| 4,992,418 A | 2/1991 | Katsoyannis et al. | |
| 5,008,241 A | 4/1991 | Markussen et al. | |
| 5,016,643 A | 5/1991 | Applegate et al. | |
| 5,028,587 A | 7/1991 | Dörschug et al. | |
| 5,049,547 A | 9/1991 | Hruby et al. | |
| 5,516,651 A | 5/1996 | Goldring et al. | |
| 5,622,839 A | 4/1997 | Moore et al. | |
| 5,674,689 A | 10/1997 | Moore et al. | |
| 5,674,981 A | 10/1997 | Moore et al. | |
| 5,683,884 A | 11/1997 | Moore et al. | |
| 5,767,131 A | 6/1998 | Gluchowski et al. | |
| 2005/0107419 A1 | 5/2005 | Bhandari et al. | |

FOREIGN PATENT DOCUMENTS

| | | |
|---|---|---|
| JP | 2001-294574 | 10/2001 |
| WO | WO 94/22829 | 10/1994 |
| WO | WO 98/37077 | 8/1998 |
| WO | WO 99/37604 | 7/1999 |

OTHER PUBLICATIONS

Nyholm et. al., Amylin Receptor Agonists: a novel pharmacological approach in the management of insulin-treated diabetes mellitus, Expert Opinion Investigational Drugs (2001) 10(9), pp. 1641-1652.*
Hcaplus 138:147070.*
Boros, E.; Cowan, D.; Cox, R.; Mebrathutu, M.; Rabinowitz, M.; Thompson, J.; Wolfe III, L. Hantzsch Synthesis of Pyrazolo[1',2':1,2] pyrazolo[3,4b] pyridines: Partial Agonists of the Calcitonin Receptor. JOC Note (2005) 70 5331-5334.
Chen, W.; Armour, S.; Way, J.; Chen, G.; Watson, C.; Irving, P.; Cobb, J.; Kadwell, S.; Beaumont, K.; Rimele,T.; Kenakin, T. Expression Cloning and Receptor Pharmacology of Human Calcitonin Receptors from MCF-7 Cells and Their Relationship to Amylin Receptors. Molecular Pharmacology (1997) 52 1164-1175.
Christopoulous, G.; Perry, K..; Morfis, M.; Tilakaratine, N., Gao, Y.; Fraser, N.; Main, M.; Foord, S.; Sexton, P. Multiple Amylin Receptors Arise from Receptor Activity-Modifying Protein Interaction with the Calcitonin Receptor Gene Product. Molecular Pharmacology (2006) 56 235-242.
Cornish, J.; Naot, D. Amylin and Adrenomedullin: Novel Regulators of Bone Growth. Current Pharmaceutical Design (2006) 8 2009-2021.
Deady, L. Ring Nitrogen Oxidation of Amino Substituted Nitrogen Heterocycles with m-Chloroperbenzoic Acid. Synthetic Communications (1997) 7 509-514.
Donnici, C.; Filho, D.; Moreia, L.; Reis, G.; Cordeiro, E.; Oliveira, I.; Carvalho, S.; Paniago, E. Synthesis of the Novel 4,4'—and 6,6'—Dihydroxamic—2,2' -Bipyridines and Mono-N-Oxide-2,2'-Bipyridine. J Braz Chem Soc (1998) 9 455-460.
Gedulin, B.; Rink, T.; Young, A. Dose-Response for Glucagonostatic Effect of Amylin in Rats. Metabolism (1997) 46 67-70.
Itoh, T.; Nagata, K.; Matsuya, Y.; Miyazaki, M.; Ohsawa, A. Reaction of Nitric Oxide with Amines. J Org Chem (1997) 62 3582-3585.
Pondel, M. Calcitonin and calcitonin receptors: bone and beyond. Int Exp Path (2000) 81 405-422.
Rushing, P.; Hagan, M.; Seeley, R.; Lutz, T. Amylin: A Novel Action in the Brain to Reduce Body Weight. Endocrinology (2000) 141 850-853.
Sexton, P.; Findlay, D.; Martin, T. Calcitonin. Current Medicinal Chemistry (1999) 6 1067-1093.
Usdin, S. Novo Develops Nasal Delivery for Insulin. BioWorld Today (Jun. 27, 1991).
Varma, R.; Kumar, D. Solid State Oxidation of 1,4-dihydropyridines to pyridines using phenyliodine (III) bis(trifluoracetate) or elemental sulfur. J Chem Soc Perkin Trans 1 (1999) 1755-1757.
Vine, W.; Beaumont, K.; Gedulin, B.; Pittner, R.; Moore, C.; Rink, T.; Young, T. Comparison of the in vitro and in vivo pharmacology of adrenomedullin, calcitonin gene-related peptide and Amylin in rats. Eur J Pharm (1996) 314 115-121.
Yadav, J.; Subba, B.; Sabitha, G.; Reddy, G. Armatization of Hantzsch 1,4-Dihydropyridines with $I_2$-MeOH$_#$. Synthesis (2000) 11 1532-1534.
Young, A.; Gedulin, B.; Vine, W.; Percy, A., Rink, T. Gastric emptying is accelerated in diabetic BB rats and is slowed by subcutaneous injections of Amylin. Diabetologia (1995) 38 642-648.

* cited by examiner

Primary Examiner—Rita J Desai
(74) Attorney, Agent, or Firm—Foley & Lardner, LLP

(57) ABSTRACT

In various aspects, the present invention relates to non-peptidic compounds, which modulate calcitonin and amylin receptor activity; to processes for the preparation of some such compounds; and to pharmaceutical compositions including such compounds. Compounds of the invention are useful as calcitonin and/or amylin agonists and in the treatment of bone diseases and metabolic diseases.

1 Claim, No Drawings

MODULATORS OF CALCITONIN AND AMYLIN RECEPTOR ACTIVITY

CROSS-REFERENCES TO RELATED APPLICATIONS

This application claims priority to U.S. Provisional Application No. 60/626,825, filed Nov. 9, 2004, the entire contents of which are herein incorporated by reference and for all purposes.

FIELD OF THE INVENTION

The present invention relates to low molecular weight compounds and pharmaceutical compositions thereof, useful as modulators of calcitonin and/or amylin receptor activity. In particular, the compounds are well suited for use as calcitonin and/or amylin receptor agonists. The invention further relates to methods of preparation and use of some such compounds and compositions in treating disorders mediated by calcitonin and amylin receptors such as bone and metabolic diseases.

BACKGROUND OF THE INVENTION

Bone is a dynamic tissue, and homeostasis in the adult skeleton requires a balance between bone resorption and bone formation. Osteoclasts and osteoblasts play a key role in this balance, with osteoclasts initiating bone resorption and osteoblasts synthesizing and depositing new bone matrix. Imbalances in bone homeostasis are associated with such disorders as osteoporosis, Paget's disease, and hyperparathyroidism.

The activities of osteoclasts and osteoblasts are regulated by complex interactions between systemic hormones such as calcitonin and the local production of growth factors and cytokines. Calcitonin, a peptide hormone secreted by the thyroid and thymus of mammals, plays an important role in maintaining bone homeostasis. Calcitonin inhibits bone resorption through binding and activation of a specific calcitonin receptor on osteoclasts [M. Pondel, Calcitonin and Calcitonin Receptors: Bone and Beyond, Int. J. Exp. Path. 81, 405-22 (2000)], with a resultant decrease in the amount of calcium released by bone into the serum. This inhibition of bone resorption has been exploited, for instance, by using calcitonin as a treatment for osteoporosis, a disease characterized by a decrease in the skeletal mass often resulting in debilitating and painful fractures. Calcitonin is also used in the treatment of Paget's disease where it provides rapid relief from bone pain, which is frequently the primary symptom associated with this disease. This analgesic effect has also been demonstrated in patients with osteoporosis or metastatic bone disease and has been reported to relieve pain associated with diabetic neuropathy, cancer, migraine and post-hysterectomy. Reduction in bone pain occurs before the reduction of bone resorption.

Despite the frequent use of animal-derived calcitonin in humans (such as salmon calcitonin), there are many disadvantages. For treatment of osteoporosis, for instance, daily prophylactic administration can be required for 5 or more years at a relatively high cost. In the United States, calcitonin is often administered by injection, and since the disease indications for this drug are not usually life threatening, patient compliance can be low. Resistance to calcitonin therapy may occur with long-term use. In addition, some patients develop antibodies to non-human calcitonin. Such disadvantages have spurred the search for small-molecule replacements for calcitonin.

Amylin and adrenomedullin are related peptides with some homology to both calcitonin and calcitonin gene-related peptide. [P M. Sexton et al., Curr. Med. Chemistry, 1999, 6:1067] Like the peptides themselves, the receptors for the calcitonin family are related to each other. Each peptide acts through its own distinct high affinity receptor, as well as through other receptors of the family, usually with lower affinity. Amylin and adrenomedullin have recently been found to stimulate the proliferation of osteoblasts in vitro, and to increase indices of bone formation when administered either locally or systemically in vivo. Furthermore, amylin inhibits bone resorption. [Cornish, J. et al., Curr. Pharm. Des., 2002, 8(23):2009]. In addition to its bone-effects, however, amylin also has an important role in postprandial glucose regulation. The neuroendocrine hormone is cosecreted with insulin at mealtimes and has been shown to suppress postprandial glucagon secretion [Gedulin, B. et al., Metabolism, 1997, 46:67], to regulate gastric emptying [Young, A. et al., Diabetologia, 1995, 38:642] and to reduce food intake [Rushing et al., Endocrinology, 2000, 141:850]. Because of these effects, the peptide and related analogues such as pramlintide are being investigated for the treatment of diabetes. Similar to calcitonin, the drawback to this peptidic approach is the need for administration by injection, resulting in potentially reduced patient compliance and high costs of production.

SUMMARY OF THE INVENTION

In various aspects, the present invention relates in part to compounds which are substituted pyridines, including compounds of Formula I; to processes for preparing such compounds; to pharmaceutical compositions including such compounds; and to methods of use and treatment with such compounds. More specifically, tetra- or pentasubstituted pyridine rings are provided for use in the treatment disorders mediated by calcitonin and/or amylin. The invention also relates to small molecule calcitonin and/or amylin modulators and to methods of treating conditions mediated by calcitonin and/or amylin using small molecule calcitonin and/or amylin modulators.

Thus, there are provided compounds having Formula I,

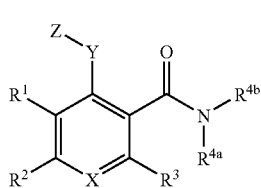

stereoisomers thereof, tautomers thereof, solvates thereof, prodrugs thereof, and pharmaceutically acceptable salts thereof; wherein X is N or NO;

Y is a divalent substituted or unsubstituted aryl, heterocyclyl, or cycloalkyl group;

Z is $-C(O)OR^5$, $-C(O)NR^6R^7$, $-NR^6C(O)R^5$, $-NR^6C(O)NR^6R^7$, $-C(O)R^5$, $-NR^6R^7$, $-OR^8$, $-SO_2NR^6R^7$, $-NR^6SO_2R^5$, or $-S(O)_mR^5$;

$R^1$ is $-H$, $-C(O)OR^9$, $-C(O)NR^{10}R^{11}$, $-CN$, $-C(O)R^9$, or $-NR^{10}C(O)R^9$;

$R^2$ is $-(C_{1-2}$ alkyl$)-R^{12}$, wherein the $C_{1-2}$ alkyl is substituted or unsubstituted;

$R^3$ is a $C_{2-6}$ branched or unbranched alkyl group, optionally substituted with one or more F;

$R^{4a}$ and $R^{4b}$ are each independently $-H$ or substituted or unsubstituted $C_{1-4}$ alkyl group;

$R^5$ is a substituted or unsubstituted aralkyl, heteroaralkyl, heterocyclylalkyl, or cycloalkyl alkyl group;

$R^6$ and $R^7$ are each independently $-H$ or a substituted or unsubstituted aralkyl, heteroaralkyl, heterocyclylalkyl, or cycloalkyl alkyl group; or $R^6$ and $R^7$, when attached to the same atom, together form a substituted or unsubstituted heterocyclyl group;

$R^8$ is a substituted or unsubstituted, branched or unbranched $C_{2-6}$ alkyl, $C_{2-6}$ alkenyl, $C_{2-6}$ alkynyl, or $C_{7-10}$ aralkyl group;

$R^9$ is —H or a substituted or unsubstituted alkyl, heteroalkyl, alkenyl, alkynyl, aryl, aralkyl, heterocyclyl, or heterocyclylalkyl group;

$R^{10}$ and $R^{11}$ are each independently —H or a substituted or unsubstituted alkyl, heteroalkyl, alkenyl, alkynyl, aryl, aralkyl, heterocyclyl, or heterocyclylalkyl group; or $R^{10}$ and $R^{11}$, when attached to the same atom, together form a substituted or unsubstituted heterocyclyl group;

$R^{12}$ is a substituted or unsubstituted cycloalkyl, aryl, heteroaryl group, or is an unsubstituted alkyl group; and m is 0, 1 or 2.

As indicated by Formula I, compounds of the invention include substituted pyridine rings (X is N) and the N-oxides thereof. In some embodiments of compounds of Formula I, Y is a divalent substituted or unsubstituted aryl or heterocyclyl group. By divalent it is meant that Y is attached to both Z and the pyridine ring as indicated in Formula I. Typically, Y is a divalent unsubstituted aryl or heteroaryl group, e.g., a divalent phenyl or pyridinyl group.

In other embodiments of compounds of Formula I, Z is —C(O)OR$^5$, —C(O)NR$^6$R$^7$, —NR$^6$C(O)R$^5$, —C(O)R$^5$, —OR$^8$, —SO$_2$NR$^6$R$^7$, —NR$_6$R$_7$SO$_2$R$_5$, or —S(O)$_m$R$^5$. Alternatively, Z can be —C(O)OR$^5$, —C(O)NR$^6$R$^7$, or —OR$^8$.

As shown above, compounds of Formula I are substituted with $R^1$ and $R^2$. In some embodiments $R^1$ is —H, —C(O)OR$^9$, or —C(O)NR$^{10}$R$^{11}$. In other embodiments, $R^9$, $R^{10}$ and $R^{11}$ are each independently —H, methyl, ethyl, n-propyl, n-butyl, isobutyl, sec-butyl, tert-butyl, cyclopentyl, or allyl. In still other embodiments, $R^2$ is —CH$_2$—CH$_2$—R$^{12}$. Exemplary groups contemplated for use as $R^{12}$ include a substituted or unsubstituted cyclohexyl, cyclopentyl, phenyl, isobutyl, or t-butyl groups. For example, $R^{12}$ is cyclohexyl, cyclopentyl, phenyl, 4-fluorophenyl, 4-trifluoromethylphenyl, isobutyl, or t-butyl.

In certain embodiments, compounds of Formula I have the Formula II:

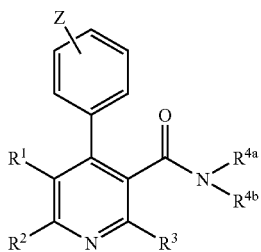

II

In such compounds, the variables Z, $R^1$, $R^2$, $R^{4a}$ and $R^{4b}$ are as defined for compounds of Formula I. In some such embodiments, Z is —C(O)OR$^5$, —C(O)NR$^6$R$^7$, or —OR$^8$.

Representative compounds of the invention include

5-Carbamoyl-2-[2-(4-fluoro-phenyl)-ethyl]-4-{4-[(furan-2-ylmethyl)-carbamoyl]-phenyl}-6-propyl-nicotinic acid ethyl ester;

5-Carbamoyl-2-(2-cyclohexyl-ethyl)-4-{4-[(furan-2-ylmethyl)-carbamoyl]-phenyl}-6-isobutyl-nicotinic acid ethyl ester;

5-Carbamoyl-2-[2-(4-fluoro-phenyl)-ethyl]-4-{4-[(furan-2-ylmethyl)-carbamoyl]-phenyl}-6-isobutyl-nicotinic acid ethyl ester;

5-Carbamoyl-2-(2-cyclohexyl-ethyl)-4-{4-[(furan-2-ylmethyl)-carbamoyl]-phenyl}-6-propyl-nicotinic acid ethyl ester;

5-Carbamoyl-2-[2-(4-fluoro-phenyl)-ethyl]-6-propyl-4-{4-[(pyridin-3-ylmethyl)-carbamoyl]-phenyl}-nicotinic acid ethyl ester;

5-Carbamoyl-2-(2-cyclohexyl-ethyl)-6-propyl-4-{4-[(pyridin-3-ylmethyl)-carbamoyl]-phenyl}-nicotinic acid ethyl ester;

2-[2-(4-Fluoro-phenyl)-ethyl]-4-{4-[(furan-2-ylmethyl)-carbamoyl]-phenyl}-6-isobutyl-pyridine-3,5-dicarboxylic acid diamide;

5-Carbamoyl-6-ethyl-2-[2-(4-fluoro-phenyl)-ethyl]-4-{4-[(furan-2-ylmethyl)-carbamoyl]-phenyl}-nicotinic acid ethyl ester; and 5-Carbamoyl-2-[2-(4-fluoro-phenyl)-ethyl]-6-isobutyl-4-{4-[(pyridin-3-ylmethyl)-carbamoyl]-phenyl}-nicotinic acid ethyl ester.

In still another aspect, there are further provided tetra- and pentasubstituted pyridine compounds that are agonists of the calcitonin receptor, the amylin receptor, or both. This aspect of the invention includes compounds of Formula I, stereoisomers thereof, tautomers thereof, solvates thereof, prodrugs thereof, and pharmaceutically acceptable salts thereof; wherein X is N or NO;

Y is a divalent substituted or unsubstituted aryl, heterocyclyl, or cycloalkyl group;

Z is —C(O)OR$^5$, —C(O)NR$^6$R$^7$, —NR$^6$C(O)R$^5$, —NR$^6$C(O)NR$^6$R$^7$, —C(O)R$^5$, —NR$^6$R$^7$, —OR$^8$, —SO$_2$NR$^6$R$^7$, —NR$^6$SO$_2$R$^5$, or —S(O)$_m$R$^5$;

$R^1$ is —H, —C(O)OR$^9$, —C(O)NR$^{10}$R$^{11}$, —CN, —C(O)R$^9$, or —NR$^{10}$C(O)R$^9$;

$R^2$ is —(C$_{1-2}$ alkyl)-R$^{12}$, wherein the $C_{1-2}$ alkyl is substituted or unsubstituted;

$R^3$ is a $C_{2-6}$ branched or unbranched alkyl group, optionally substituted with one or more F;

$R^{4a}$ and $R^{4b}$ are each independently —H or substituted or unsubstituted $C_{1-4}$ alkyl group;

$R^5$ is a substituted or unsubstituted aralkyl, heteroaralkyl, heterocyclylalkyl, or cycloalkyl alkyl group;

$R^6$ and $R^7$ are each independently —H or a substituted or unsubstituted aralkyl, heteroaralkyl, heterocyclylalkyl, or cycloalkyl alkyl group; or $R^6$ and $R^7$, when attached to the same atom, together form a substituted or unsubstituted heterocyclyl group;

$R^8$ is a substituted or unsubstituted, branched or unbranched $C_{2-6}$ alkyl, $C_{2-6}$ alkenyl, $C_{2-6}$ alkynyl, or $C_{7-10}$ aralkyl group;

$R^9$ is —H or a substituted or unsubstituted alkyl, heteroalkyl, alkenyl, alkynyl, aryl, aralkyl, heterocyclyl, or heterocyclylalkyl group;

$R^{10}$ and $R^{11}$ are each independently —H or a substituted or unsubstituted alkyl, heteroalkyl, alkenyl, alkynyl, aryl, aralkyl, heterocyclyl, or heterocyclylalkyl group; or $R^{10}$ and $R^{11}$, when attached to the same atom, together form a substituted or unsubstituted heterocyclyl group;

$R^{12}$ is a substituted or unsubstituted cycloalkyl, aryl, heteroaryl group, or is an unsubstituted alkyl group; and m is 0, 1 or 2.

In another aspect, the invention provides methods of preparing compounds of Formula I. For example, when X is N in Formula I, the methods include exposing a compound of Formula III to a first oxidant that selectively oxidizes a dihydropyridinyl ring to a pyridinyl ring,

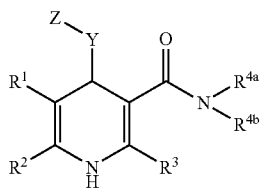

thereby providing a compound of Formula IA

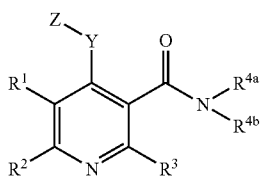

wherein Y, Z, $R^1$, $R^2$, $R^3$, $R^{4a}$ and $R^{4b}$ are as defined previously.

Suitable first oxidants for use in the transformation of III to IA include ceric (IV) ammonium nitrate (CAN), 2,3-dichloro-5,6-dicyano-1,4-benzoquinone (DDQ), Pd/acetic acid, [bis(trifluoroacetoxy)iodo]benzene and the like. In some embodiments of the method, Y is an unsubstituted divalent phenyl or pyridinyl group. In others, Z is —C(O)$OR^5$, —C(O)$NR^6R^7$, or —$OR^8$.

In some embodiments of methods of making compounds of Formula I, the methods include the step of preparing the compound of Formula III by reacting Z—Y—CHO, $R^1$CH=C(NH$_2$)$R^2$, and $R^3$C(=NH)—CH$_2$—C(O)—$NR^{4a}R^{4b}$ in a solvent. Typically this solvent is an alkyl alcohol, such as ethanol, methanol, isopropanol and the like. Alternatively, the methods include the step of preparing the compound of Formula III by reacting Z—Y—CHO, $R^1$—CH$_2$—C(O)$R^2$ and $R^3$—C(O)—CH$_2$—C(O)—$NR^{4a}R^{4b}$ in the presence of ammonia to provide the compound of Formula III. In these methods, any suitable source of ammonia may be used such as but not limited to ammonium hydroxide, ammonium acetate, or ammonium carbonate.

The methods of making compounds of Formula I may further include the step of exposing the compound of Formula IA to a second oxidant that selectively oxidizes the pyridinyl N to an N-oxide, thereby providing a compound of Formula IB:

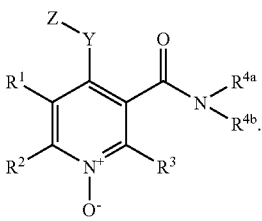

Second oxidants that may be used include but are not limited to hydrogen peroxide and m-chloroperbenzoic acid (MCPBA).

In accordance with yet another aspect of the invention, there are provided pharmaceutical compositions comprising a compound as described herein (e.g., a tetra- or pentasubstituted pyridine, and/or a compound of Formulas I, IA, IB, or II, or compounds having amylin and/or calcitonin agonist activity as defined herein) and a pharmaceutically acceptable carrier.

There are further provided methods of modulating the activity of a calcitonin and/or amylin receptor, the method comprising contacting the calcitonin and/or amylin receptor with a compound as described herein. The compound is typically an agonist at the calcitonin and/or amylin receptor.

In yet another aspect, there is provided a method of modulating the activity of a calcitonin or amylin receptor, the method comprising administering an effective amount of a compound of the invention to a subject.

In accordance with yet another aspect of the invention, there are provided compounds having calcitonin agonist or calcitonin and amylin agonist activity, wherein the compounds are non-peptidic, and wherein the compounds have an agonist effect in T47D cells endogenously expressing the calcitonin receptor, with a maximal efficacy greater than 20% of the efficacy of the human calcitonin peptide. In some such embodiments the compound has an agonist effect with a maximal efficacy greater than 25%, greater than 30% or greater than 40% of the efficacy of the human calcitonin peptide. In some other such embodiments, the compound has a molecular weight of less than 1000 Da. In yet other such embodiments, the compound has a molecular weight of less than 800 Da, or of less than 600 Da.

There are further provided compounds having calcitonin agonist, or calcitonin and amylin agonist activity, wherein the compounds are non-peptidic, and wherein the compounds have an agonist effect in HEK-293 cells recombinantly expressing the rat calcitonin receptor, with an $EC_{50}$ less than the $EC_{50}$ of 2-[2-(4-fluoro-phenyl)-ethyl]-4-{4-[(furan-2-ylmethyl)-carbamoyl]-phenyl}-7-isopropyl-5-oxo-6,7-dihydro-5H-pyrrolo[3,4-b]pyridine-3-carboxylic acid ethyl ester. In some such embodiments, the compounds have an agonist effect in T47D cells endogenously expressing the calcitonin receptor, with a maximal efficacy greater than 20% of the efficacy of the human calcitonin peptide. In some such embodiments, the compound has a molecular weight of less than 1000 Da. In others, the compound has a molecular weight of less than 800 Da, or less than 600 Da.

Also contemplated are compounds having amylin agonist or amylin and calcitonin agonist activity, wherein the compounds are non-peptidic, and wherein the compounds have an agonist effect in HEK-293 cells recombinantly expressing the rat amylin receptor, with an $EC_{50}$ less than the $EC_{50}$ of 2-[2-(4-fluoro-phenyl)-ethyl]-4-{4-[(furan-2-ylmethyl)-carbamoyl]-phenyl}-7-isopropyl-5-oxo-6,7-dihydro-5H-pyrrolo[3,4-b]pyridine-3-carboxylic acid ethyl ester. In some such embodiments, the compounds have an agonist effect in T47D cells endogenously expressing the calcitonin receptor, with a maximal efficacy greater than 20% of the efficacy of the human calcitonin peptide. In other such embodiments, the compounds have an agonist effect in HEK-293 cells recombinantly expressing the rat calcitonin receptor, with an $EC_{50}$ less than the $EC_{50}$ of 2-[2-(4-fluoro-phenyl)-ethyl]-4-{4-[(furan-2-ylmethyl)-carbamoyl]-phenyl}-7-isopropyl-5-oxo-6,7-dihydro-5H-pyrrolo[3,4-b]pyridine-3-carboxylic acid ethyl ester. In some such embodiments, the compound has an agonist effect in T47D cells endogenously expressing the calcitonin receptor, with a maximal efficacy greater than 20% of the efficacy of the human calcitonin peptide. In yet other embodiments, the compound has a molecular weight of less than 1000 Da. In still others, the compound has a molecular weight of less than 800 Da, or less than 600 Da.

In some embodiments of compounds having calcitonin agonist activity, amylin agonist activity, or calcitonin and amylin agonist activity, a fused pyridine ring is not within the chemical structure of the compound. In other embodiments, the compounds do not comprise a 6,7-dihydro-pyrrolo[3,4-b]pyridin-5-one; a 1,2-dihydro-pyrazolo[3,4-b]pyridin-3-one; a 7,8-dihydro-6H-quinolin-5-one; a 7,8-dihydro-6H-[1,6]naphthyridin-5-one; or a 7,8-dihydro-6H-pyrido[2,3-d]pyridazin-5-one substructure. In yet others, the compound comprises a pentasubstituted, non-fused pyridine ring. Any combination of these embodiments is also possible.

In a further aspect, the invention provides methods of treating a disorder mediated by calcitonin and/or amylin receptors, the method comprising administering to a subject in need thereof a therapeutically effective amount of a compound as described herein. (e.g., a tetra- or pentasubstituted pyridine, and/or a compound of Formulas I, IA, IB, or II, or compounds having amylin and/or calcitonin agonist activity as defined herein). In some such embodiments the compound administered is a calcitonin and/or amylin receptor agonist. Thus, compounds of the invention may be used to treat bone disorders, metabolic disorders, pain, and other disorders. Exemplary bone disorders include osteoporosis, Paget's disease, hypercalcemia, Sudeck's atrophy, polystatic fibrous displasia, intersemocostoclavicular ossification, osteogenesis imperfecta, osteopenia, periodontal disease or defect, osteolytic bone disease, metastatic bone disorder, or bone loss resulting from malignancy, autoimmune arthritides, breakage and fracture, immobility and disuse. In some such embodiments, the bone disorder is osteoporosis or Paget's disease. Types of pain that may be treated using inventive compounds include osteopathic pain, phantom limb pain, general pain, hyperalgesia, pain associated with pancreatitis, and pain associated with diabetic neuropathy. Exemplary metabolic disorders include insulin dependent diabetes, non-insulin dependent diabetes, impaired glucose tolerance, obesity, syndrome X, diabetes mellitus, hypoglycemia, hyperglycemia, postprandial hyperglycemia, or an insulin-requiring disorder other than diabetes mellitus or and diabetic complications. Other disorders amenable to treatment with inventive compounds include primary or secondary hyperthyroidism, endocrine disorder, conditions associated with inhibiting gastric secretion, gastrointestinal disorders, gastritis, gastric ulceration, postprandial dumping syndrome, renal osteodystrophy, male infertility, and pancreatitis.

Compounds of the invention can be used in combination with other therapies. In particular, compounds of this invention can be combined with insulin for the treatment of diabetes mellitus and other insulin-requiring states. By "insulin" is meant a polypeptide or its equivalent useful in regulation of blood glucose levels. A general description of such insulins is provided in Goodman and Gilman's The Pharmacological Basis of Therapeutics, 8th Ed., Pergamon Press (1990). Such insulins can be fast acting, intermediate acting, or long acting. Various derivatives of insulin exist and are useful in this invention. See, e.g., U.S. Pat. Nos. 5,049,547, 5,028,587, and 5,016,643. Insulin peptides are also useful (see, e.g., U.S. Pat. No. 5,008,241), as are analogues (see, e.g., U.S. Pat. Nos. 4,992,417 and 4,992,418). Such compositions can be administered by any standard route, including nasal administration (see, e.g., U.S. Pat. Nos. 4,988,512 and 4,985,242, and 2 BioWorld Today, No. 125 (1991)). The compounds of this invention are also useful in combination with a glucagon for the prevention and treatment of hypoglycemia. See Young et al., U.S. application Ser. No. 07/640,478, filed Jan. 10, 1991, entitled "Hyperglycemic Compositions."

In yet another aspect of the invention, there is provided a method of increasing muscle mass or changing body composition, the method comprising administering to a subject in need thereof a therapeutically effective amount of a compound of the invention.

Also provided is a method of reducing gastric motility, for example associated with a gastrointestinal disorder such as spasm, or delaying gastric emptying, the method comprising administering to a subject in need thereof a therapeutically effective amount of a compound as described herein. In some such embodiments, the subject is undergoing a gastrointestinal diagnostic procedure, for example, a radiological examination or magnetic resonance imaging.

In yet another aspect of the invention, there is provided a method of treating or preventing pain, fever, inflammation, arthritis, hypercoagulability, or other condition for which a non-steroidal anti-inflammatory agent would be indicated, the method comprising administering to a subject in need thereof a therapeutically effective amount of a compound of the invention and a therapeutically effective amount of a non-steroidal anti-inflammatory agent.

Additionally, there is provided a method of enhancing the analgesic activity of a non-steroidal anti-inflammatory drug in a subject, the method comprising administering a compound as described herein along with said anti-inflammatory drug. Examples of non-steroidal anti-inflammatory agent useful in the methods above are salicylate, phenylbutazone, indomethacin, acetaminophen, phenacetin, naproxen, or ibuprofen.

Also provided is a pharmaceutical composition comprising (1) a compound of claim 1, or a pharmaceutically acceptable salt, prodrug, or solvate thereof, and (2) a non-steroidal anti-inflammatory agent, in a pharmaceutically acceptable carrier and dose. In some such embodiments, the non-steroidal anti-inflammatory agent is selected from the group consisting of salicylate, phenylbutazone, indomethacin, acetaminophen, phenacetin, naproxen, and ibuprofen.

In yet another aspect of the invention, there is provided a method of treating a disorder mediated by an amylin receptor, the method comprising administering to a subject in need thereof a therapeutically effective amount of an amylin agonist, wherein the amylin agonist is a non-peptidic compound, provided the amylin agonist does not comprise a 6,7-dihydro-pyrrolo[3,4-b]pyridin-5-one or a 7,8-dihydro-6H-quinolin-5-one substructure. In some such embodiments, the amylin agonist has a molecular weight below 1000 Da. In others, the amylin agonist has a molecular weight of less than 800 Da, or less than 600 Da. In other such embodiments, the amylin agonist has an agonist effect in HEK-293 cells recombinantly expressing the rat amylin receptor, with an $EC_{50}$ less than the $EC_{50}$ of 2-[2-(4-fluoro-phenyl)-ethyl]-4-{4-[(furan-2-ylmethyl)-carbamoyl]-phenyl}-7-isopropyl-5-oxo-6,7-dihydro-5H-pyrrolo[3,4-b]pyridine-3-carboxylic acid ethyl ester. In some such embodiments, the amylin agonist has an agonist effect in HEK-293 cells recombinantly expressing the rat calcitonin receptor, with an $EC_{50}$ less than the $EC_{50}$ of 2-[2-(4-fluoro-phenyl)-ethyl]-4-{4-[(furan-2-ylmethyl)-carbamoyl]-phenyl}-7-isopropyl-5-oxo-6,7-dihydro-5H-pyrrolo[3,4-b]pyridine-3-carboxylic acid ethyl ester. In some of those embodiments, the amylin agonist has an agonist effect in T47D cells endogenously expressing the calcitonin receptor, with a maximal efficacy greater than 20% of the efficacy of the human calcitonin peptide. Any combination of these embodiments is also possible.

In some other embodiments of the method of treating a disorder mediated by an amylin receptor, the amylin agonist has an agonist effect in HEK-293 cells recombinantly expressing the rat calcitonin receptor, with an $EC_{50}$ less than the $EC_{50}$ of 2-[2-(4-fluoro-phenyl)-ethyl]-4-{4-[(furan-2-ylmethyl)-carbamoyl]-phenyl}-7-isopropyl-5-oxo-6,7-dihydro-5H-pyrrolo[3,4-b]pyridine-3-carboxylic acid ethyl ester. In some such embodiments, the amylin agonist has an agonist effect in T47D cells endogenously expressing the calcitonin receptor, with a maximal efficacy greater than 20% of the efficacy of the human calcitonin peptide. Any combination of these embodiments is also possible.

In some other embodiments of the method of treating a disorder mediated by an amylin receptor, the amylin agonist has an agonist effect in T47D cells endogenously expressing the calcitonin receptor, with a maximal efficacy greater than 20% of the efficacy of the human calcitonin peptide. In some such embodiments the amylin agonist has an agonist effect with a maximal efficacy greater than 25% of the efficacy of the human calcitonin peptide. In others, the amylin agonist has an agonist effect with a maximal efficacy greater than 30% or greater than 40% of the efficacy of the human calcitonin peptide. Any combination of these embodiments is also possible.

In yet other embodiments of the method of treating a disorder mediated by an amylin receptor, a fused pyridine ring is not within the chemical structure of the amylin agonist. In still others, the amylin agonist does not comprise a 1,2-dihydropyrazolo[3,4-b]pyridin-3-one; a 7,8-dihydro-6H-[1,6]naphthyridin-5-one; or a 7,8-dihydro-6H-pyrido[2,3-d]pyridazin-5-one substructure. In additional embodiments, the amylin agonist comprises a pentasubstituted, non-fused pyridine ring. In yet other embodiments, the amylin agonist is a compound of Formula I. Any combination of these embodiments is also possible.

DETAILED DESCRIPTION OF THE INVENTION

The following definitions are used throughout this specification.

Generally, reference to a certain element such as hydrogen or H is meant to include all isotopes of that element. For example, if an R group is defined to include hydrogen or H, it also includes deuterium and tritium. Hence, isotopically labeled compounds are within the scope of the invention.

In general, "substituted" refers to a functional group as defined below in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Examples of substituent groups are, but not limited to: halogens (i.e., F, Cl, Br, and I); hydroxyls; alkoxy, aryloxy, aralkyloxy, heterocyclyloxy, and heterocyclylalkoxy groups; carbonyls(oxo); carboxyls; esters; urethanes; oximes; hydroxylamines; thiols; alkyl, aryl, aralkyl, heterocyclyl and heterocyclylalkyl sulfide groups; sulfoxides; sulfones; sulfonyls; sulfonamides; amines; N-oxides; hydrazides; hydrazones; azides; amides; ureas; amidines; guanidines; enamines; imides; isocyanates; imines; hydroxyimines; and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with alkyl, alkenyl, and alkynyl groups as defined below.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with any of the groups listed above, for example, amino, oxo, hydroxy, cyano, carboxy, nitro, thio, alkoxy, and F, Cl, Br, I groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include mono-, bicyclic and polycyclic ring systems, such as, for example bridged cycloalkyl groups as described below, and fused rings, such as, but not limited to, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with any of the groups listed above, for example, methyl, amino, hydroxy, cyano, carboxy, nitro, thio, alkoxy, and F, Cl, Br; I groups.

Bridged cycloalkyl groups are cycloalkyl groups in which two or more hydrogen atoms are replaced by an alkylene brige, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with any of the groups listed above, for example, amino, hydroxy, cyano, carboxy, nitro, thio, alkoxy, and F, Cl, Br, I groups.

Cycloalkyl alkyl groups are alkyl groups as defined above in which a hydrogen or carbon bond of an alkyl group is replaced with a bond to a cycloalkyl group as defined above.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl, among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups.

Cycloalkenylalkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons in the ring portions of the groups, and in others from 6 to 12 or even 6-10 carbon atoms. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with groups such as those listed above.

Aralkyl groups are alkyl groups as defined above in which a hydrogen or carbon bond of an alkyl group is replaced with a bond to an aryl group as defined above. Representative aralkyl groups include but are not limited to benzyl and phenethyl groups and fused (cycloalkylaryl)alkyl groups such as 4-ethyl-indanyl.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 10, 12, or 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, pyrrolidinyl, pyrrolinyl, imidazolyl, imidazolinyl, imidazolidinyl, piperidinyl, piperazinyl, morpholinyl, pyrrolyl, pyrazolyl, pyrazolidinyl, tetrahydropyranyl, thiomorpholinyl, triazolyl, tetrazolyl, oxazolyl, isoxazolyl, thiazolyl, pyridinyl, pyrimidinyl, pyridazinyl, pyrazinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, quinazolinyl, benzotriazolyl, 2,3-dihydrobenzo[1,4]dioxinyl, and benzo[1,3]dioxolyl groups. Representative substituted heterocyclyl groups may be mono-substituted or substituted more than once, such as, but not limited to, pyridinyl or morpholinyl groups, which are 2-, 3-, 4-, 5-, or 6-substituted, or disubstituted with various groups as defined above, including, but not limited to, alkyl, oxo, carbonyl, amino, alkoxy, cyano, and/or halo.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, benzofuranyl, indolyl, azaindolyl, indazolyl, benzimidazolyl, azabenzimidazolyl, benzotriazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups". Representative substituted heteroaryl groups may be substituted one or more times with various groups as defined above, including, but not limited to, amino, oxo, alkoxy, alkyl, cyano, and/or halo.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, 4-ethyl-morpholinyl, 4-propylmorpholinyl, furan-2-yl methyl, furan-3-yl methyl, pyridine-3-yl methyl, tetrahydrofuran-2-yl ethyl, and indol-2-yl propyl.

Heteroaralkyl groups are alkyl groups as defined above in which a hydrogen or carbon bond of an alkyl group is replaced with a bond to a heteroaryl group as defined above.

Alkoxy groups are hydroxyl groups (—OH) in which the bond to the hydrogen atom is replaced by a bond to a carbon atom of an alkyl group as defined above. Examples of linear alkoxy groups include but are not limited to methoxy, ethoxy, propoxy, butoxy, pentoxy, hexoxy, and the like. Examples of branched alkoxy include but are not limited to isopropoxy, sec-butoxy, tert-butoxy, isopentoxy, isohexoxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl. Examples include but are not limited to phenoxy, naphthyloxy, and benzyloxy.

The term "carboxylate" as used herein refers to a —COOH group.

The term "carboxylic ester" as used herein refers to —COOR$^{27}$ groups. R$^{27}$ is a substituted or unsubstituted alkyl, cycloalkyl, alkenyl, aryl, aralkyl, heterocyclylalkyl or heterocyclyl group as defined herein.

The term "amide" (or "amido") includes C- and N-amide groups, i.e., —C(O)NR$^{28}$R$^{29}$, and —NR$^{28}$C(O)R$^{29}$ groups, respectively. R$^{28}$ and R$^{29}$ are independently hydrogen, or a substituted or unsubstituted alkyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H).

Urethane groups include N- and O-urethane groups, i.e., —NR$^{30}$C(O)OR$^{31}$ and —OC(O)NR$^{30}$R$^{31}$ groups, respectively. R$^{30}$ and R$^{31}$ are independently hydrogen, or a substituted or unsubstituted alkyl, cycloalkyl, aryl, aralkyl, heterocyclylalkyl, or heterocyclyl group as defined herein.

The term "amine" as used herein refers to —NHR$^{32}$ and —NR$^{33}$R$^{34}$ groups, wherein R$^{32}$, R$^{33}$ and R$^{34}$ are independently hydrogen, or a substituted or unsubstituted alkyl, cycloalkyl, aryl, aralkyl, heterocyclylalkyl or heterocyclyl group as defined herein.

The term "sulfonamido" includes S- and N-sulfonamide groups, i.e., —SO$_2$NR$^{12}$R$^{13}$ and —NR$^{12}$SO$_2$R$^{13}$ groups, respectively. R$^{12}$ and R$^{13}$ are independently hydrogen, or a substituted or unsubstituted alkyl, cycloalkyl, aryl, aralkyl, heterocyclylalkyl, or heterocyclyl group as defined herein. Sulfonamido groups therefore include but are not limited to sulfamoyl groups (—SO$_2$NH$_2$).

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylhiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; urethanes such as t-butyloxycarbonylamine, benzyloxycarbonylamine, and fluorenyloxycarbonylamine; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, ketones are typically in equilibrium with their enol forms. Thus, ketones and their enols are referred to as tautomers of each other. Also, for example, triazoles may exhibit the following isomeric forms, which are referred to as tautomers of each other:

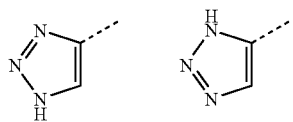

As readily understood by one skilled in the art, a wide variety of functional groups and other structures may exhibit tautomerism, and all tautomers of compounds having Formula I are within the scope of the present invention.

All chiral, diastereomeric, racemic forms and all geometric isomeric forms of a structure are intended, unless the specific stereochemistry or isomeric form is specifically indicated. Compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

The term "non-peptidic" as used throughout the specification and claims is intended to exclude any structure comprised of two or more amino acids linked together, including structures containing chemical modifications and derivatives of amino acids. The amino acids forming all or a part of a "peptidic" structure may be naturally occurring amino acids, stereoisomers and modifications of such amino acids, non-protein amino acids, post-translationally modified amino acids, enzymatically modified amino acids, protected amino acids, and the like. In some instances the peptidic structure may also include constructs or structures designed to mimic amino acids, so long as the peptidic structure contains at least one or more amino acids.

A "modulator" denotes compounds that alter the activity of a receptor, as compared to control, or as compared to expected receptor activity. As used herein, "calcitonin modulators" are compounds that alter (increase or decrease) calcitonin receptor activation and/or calcitonin receptor-mediated signal transduction. As used herein, "amylin modulators" are compounds that alter (increase or decrease) amylin receptor activation and/or amylin receptor-mediated signal transduction. A modulator may be a receptor agonist or antagonist. In certain embodiments, a receptor modulator may exhibit an EC$_{50}$ or IC$_{50}$ at a receptor that is less than 10 µM, 500 nM, 200 nM, 100 nM, 50 nM, 25 nM or 10 nM, in for example, a typical cAMP activity assay, as described herein.

An "agonist" refers to a compound that mimics one or more effects (or activity) of the receptor ligand, for example, the effects of amylin or calcitonin peptides, in vitro or in vivo. The effects of the agonist include the ability to directly or indirectly interact or bind with one or more receptors, and the resulting activation or inactivation by the agonist. Thus, "Calcitonin agonist", means a compound or molecule that has the ability to activate one or more calcitonin receptors. "Amylin agonist" means a compound or molecule that has the ability to activate one or more amylin receptors, including amylin receptor 1 (calcitonin receptor+RAMP1) or amylin receptor 2 (calcitonin receptor+RAMP3), or both. In some embodiments, a compound may be both an amylin agonist and a calcitonin agonist. In the instant invention, these effects can be assessed by, for example, the calcitonin or amylin cAMP activity assays, as described in the Examples.

"Amylin receptor" (AR) includes amylin receptor 1 (AR1) or amylin receptor 2 (AR2). "AR1" means any isoforms of amylin receptor 1 (calcitonin receptor+RAMP1) from any animal species. The definition of AR1 includes, but is not limited to, those receptors for which the cDNA or genomic sequence encoding the receptor has been deposited in a sequence database. The nucleotide and protein sequences of these receptors are available from GenBank or Derwent. "AR2" means any isoform of amylin receptor 2 (calcitonin receptor+RAMP3) from any animal species. The definition of AR2 receptor includes, but is not limited to, those receptors for which the DNA sequence encoding the receptor has been deposited in a sequence database. The nucleotide and protein sequences of these receptors are available from GenBank or Derwent.

The term "Amylin Receptor or AR" also includes truncated and/or mutated proteins wherein regions of the receptor molecule not required for ligand binding or signaling have been deleted or modified. For example one of skill in the art will recognize that an AR with one or more conservative changes in the primary amino acid sequence would be useful in the present invention. It is known in the art that substitution of certain amino acids with different amino acids with similar structure or properties (conservative substitutions) can result in a silent change, i.e., a change that does not significantly alter function. Conservative substitutes are well known in the art. For example, it is known that G-Protein Coupled Receptors (GPCRs) can tolerate substitutions of amino acid residues in the transmembrane alpha-helices, which are oriented toward lipid, with other hydrophobic amino acids, and remain functional. AR1s differing from a naturally occurring sequence by truncations and/or mutations such as conservative amino acid substitutions are also included in the definition of AR1. AR2s differing from a naturally occurring sequence by truncations and/or mutations such as conservative amino acid substitutions are also included in the definition of AR2.

One of skill in the art would also recognize that ARs from a species other than human or rat, particularly mammalian species, would be useful in the present invention. One of skill in the art would further recognize that by using probes from the known AR species' sequences, cDNA or genomic sequences homologous to the known sequence could be obtained from the same or alternate species by known cloning methods. Such AR1s are also included in the definition of AR1 and such AR2s are also included in the definition of AR2.

In addition, one of skill in the art would recognize that functional allelic variants or functional splice variants of ARs might be present in a particular species and that these variants would have utility in the present invention. Splice variants of ARs are known, for example U.S. Pat. Nos. 5,683,884, 5,674,981, 5,674,689, 5,622,839, and 5,516,651, each of which is incorporated herein by reference. Such AR1 variants are also included in the definition of AR1 and such AR2 variants are also included in the definition of AR2.

Agonist efficacy as used herein, refers to a compound's ability to activate signaling via second messenger cascades via the appropriate receptors. Typically, efficacy is quantified by measuring second messengers after contacting intact cells with the receptor modulators. Second messenger measurement includes, for example, the accumulation of intracellular cAMP in the presence of a phosphodiesterase inhibitor upon exposure to an agonist. Efficacy can be measured in many other ways (such as GTP exchange, etc.), known to those of skill in the art.

As used herein in reference to receptor agonists, "efficacy" is a measure of a compound's agonist activity specified relative to the agonist activity of a reference compound. A reference compound is typically calcitonin or amylin peptide. For example, efficacy of a calcitonin agonist test compound at the calcitonin receptor may be defined by the amount of cAMP produced in response to the test compound in T47D cells using standard assay conditions (see examples), relative to the amount of cAMP produced by a saturating concentration of human calcitonin. The amount of cAMP produced in response to a saturating concentration of human calcitonin is defined as 100% efficacy. The amount of cAMP produced in the absence of any stimulus is defined as 0% efficacy. The efficacy of a test compound is therefore:

100*([cAMP in presence of test compound]−[cAMP in absence of stimulus])/([cAMP in presence of saturating human calcitonin]−[cAMP in absence of stimulus]).

Efficacy may be determined using for example, the calcitonin cAMP activity assays, as described in the Examples. Maximal efficacy is defined as the maximal response (e.g cAMP production) measurable for a particular agonist, after which increasing concentrations of the agonist do not elicit a further increase in the response. As well known to those of skill in the art, the result of any single assay will have some variability, so that cut-offs (for example an efficacy of 20%) should be considered an average of consistent measurements.

"Treating" within the context of the instant invention, means an alleviation, in whole or in part, of symptoms associated with a disorder or disease, or halt of further progression or worsening of those symptoms, or prevention or prophylaxis of the disease or disorder. Similarly, as used herein, a "therapeutically effective amount" of a compound of the invention refers to an amount of the compound that alleviates, in whole or in part, symptoms associated with a disorder or disease, or halts of further progression or worsening of those symptoms, or prevents or provides prophylaxis for the disease or disorder. Treatment may also include administering the pharmaceutical formulations of the present invention in combination with other therapies. For example, the compounds of the invention can also be administered in conjunction with other therapeutic agents against bone disease or agents used for the treatment of metabolic disorders.

Compounds of Formula I, where Y is phenyl (e.g., Formula II) may be readily prepared using the Hantzsch reaction. For example, a compound of Formula II may readily be prepared as shown in Scheme 1. A substituted benzaldehyde, beta-keto ester, ammonium hydroxide, and a beta-keto amide may be combined in a suitable solvent such as ethanol and exposed to heat to give the dihydropyridine. The reaction can be heated by microwave radiation to shorten the reaction times. The dihydropyridine is oxidized using a suitable agent such as DDQ, CAN or [bis(trifluoroacetoxy)iodo]benzene in a solvent, such as methylene chloride or chloroform, to give the pyridine. The N-oxide may be prepared by oxidizing the pyridine nitrogen with m-chloroperbenzoic acid [see Synth. Comm. 1977, 509-14], $H_2O_2$ [J. Braz. Chem. Soc. 1998, 5:455-60] or another suitable agent. Those of skill in the art will appreciate that similar methodology can be used to readily prepare other compounds of Formula I, where Y is other aryl, or heteroaryl. Literature methods may also be modified to access compounds where Y is cycloalkyl as well as non-aromatic heterocyclyl [see, e.g., J. Chem. Soc. Perkin Trans., 1999, 1755; Synthesis, 2000, 1532; J. Org. Chem., 1997, 62:3582].

Scheme 1

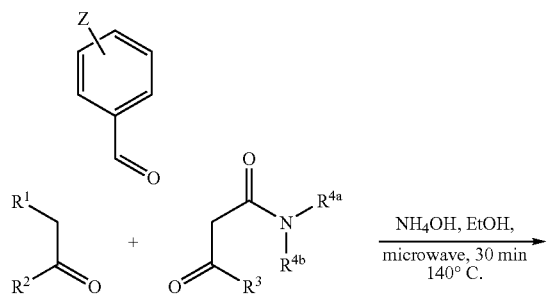

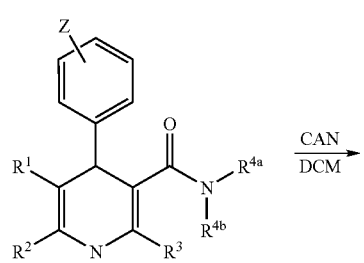

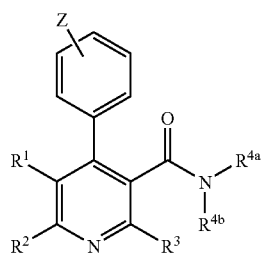

Alternatively, compounds of Formula I where Y is phenyl (e.g., Formula II) may also be prepared as shown in Scheme 2. A substituted benzaldehyde, substituted enamine and a substituted acrylamide may be combined in a suitable solvent such as ethanol and exposed to heat to give the dihydropyridine. The latter compound may be oxidized to the pyridine with CAN under acidic conditions (e.g., TFA) or other suitable oxidant as disclosed herein. Similarly, compounds of Formula I where Y is other aryl, heterocyclyl or cycloalkyl may be made by modification of the present methods or related literature methods.

Scheme 2

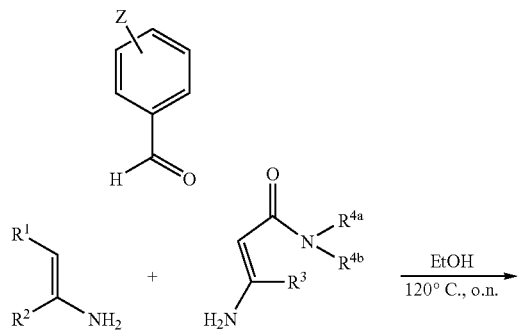

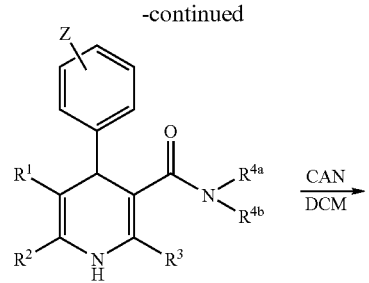

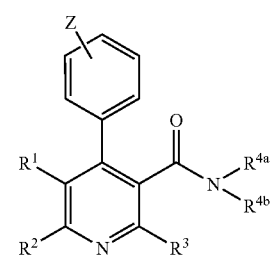

In another aspect, the instant invention also provides for pharmaceutical compositions which may be prepared by mixing one or more compounds of the invention, pharmaceutically acceptable salts thereof, stereoisomers thereof, tautomers thereof, prodrugs thereof, or solvates thereof, with pharmaceutically acceptable carriers, excipients, binders, diluents or the like to treat or ameliorate a variety of disorders mediated by calcitonin and/or amylin receptors. The compositions of the invention may be used to create formulations and prevent or treat disorders mediated by calcitonin and/or amylin receptors such as bone and metabolic diseases. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts, prodrugs thereof, or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an Ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective amount of a compound of the present invention may vary depending upon the route of administration and dosage form. The typical compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLES

The following abbreviations are used throughout the application:

| | |
|---|---|
| AcOH | Acetic acid |
| CAN | Ceric (IV) ammonium nitrate |
| DCM | Dichloromethane |
| DDQ | 2,3-Dichloro-5,6-Dicyano-1,4-benzoquinone |
| DMAP | 4-N,N-dimethylaminopyridine |
| EDCI | 1-[3-(Dimethylamino)propyl]-3-ethyl-carbodiimide |
| EtOH | Ethanol |
| EtOAc | Ethyl acetate |
| LC/MS | Liquid chromatography mass spectroscopy |
| MeOH | Methanol |
| PhMe | Toluene |
| RAMP | Receptor activity-modifying protein |
| r.t. | Room temperature |
| R.T. | Retention time |

Example 1

Synthesis of Ethyl 3-amino-5-(4-fluorophenyl)-2-pentenoate (4)

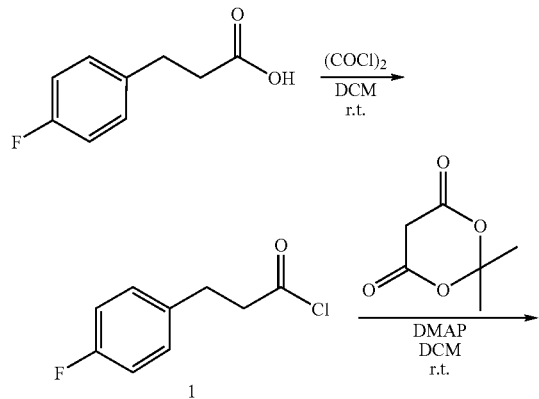

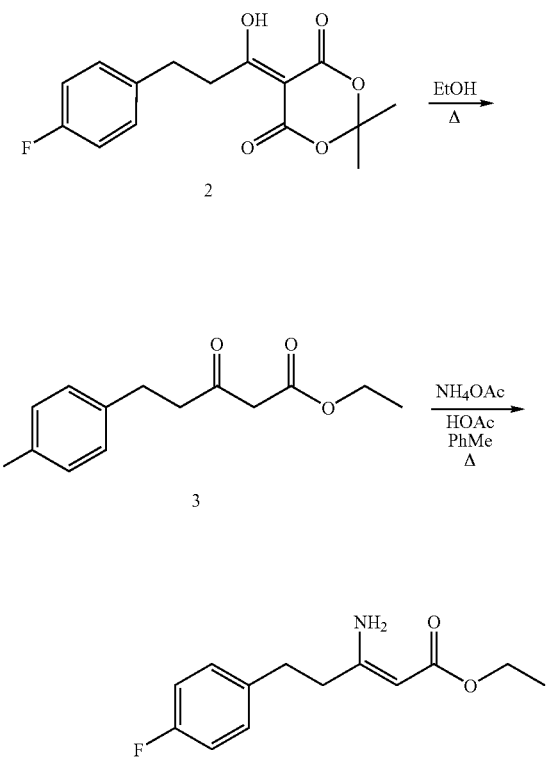

Oxalyl chloride (31 mL, 357 mmol) was added to a solution of 3-(4-fluorophenyl)propionic acid (20 g, 119 mmol) in dichloromethane (100 mL) and the mixture was stirred overnight at r.t. After concentrating in vacuo and drying in high vacuum, the crude acid chloride 1 was added dropwise to a cooled solution of Meldrum's acid (18.86 g, 131 mmol, 1.1 eq) and 4-N,N-dimethylaminopyridine (DMAP, 15.99 g, 131 mmol, 1.1 eq) in dichloromethane (100 mL) at 0° C. and the resulting mixture was stirred overnight at r.t. The solvent was evaporated in vacuo, ethyl acetate (150 mL) was added and the solution was washed with water (150 mL), 1 M aqueous HCl (3×150 mL) and brine (150 mL). The organic layer was dried over $Na_2SO_4$, concentrated in vacuo and dried in high vacuum to give crude compound 2 as an oil which was dissolved in ethanol (200 mL). The solution was heated to reflux overnight. After concentrating in vacuo and drying in high vacuum, the crude compound 3 was added to a mixture of ammonium acetate (45.86 g, 595 mmol), acetic acid (6.9 mL, 119 mmol) and toluene (220 mL). After heating to reflux overnight with azeotropic removal of water, the solvent was removed in vacuo. Silica gel column chromatography (hexane—20% ethyl acetate/hexane) yielded the title compound (7.7 g, 27% yield for 4 steps) as a pale yellow oil. $^1$H NMR (400 MHz, $CDCl_3$): δ 1.28 (t, 3H), 2.41 (t, 2H), 2.86 (t, 2H), 4.13 (q, 2H), 4.58 (s, 1H), 7.00 (m, 2H), 7.16 (m, 2H).

Example 2

Synthesis of 4-Formyl-N-furan-2-ylmethylbenzamide (6)

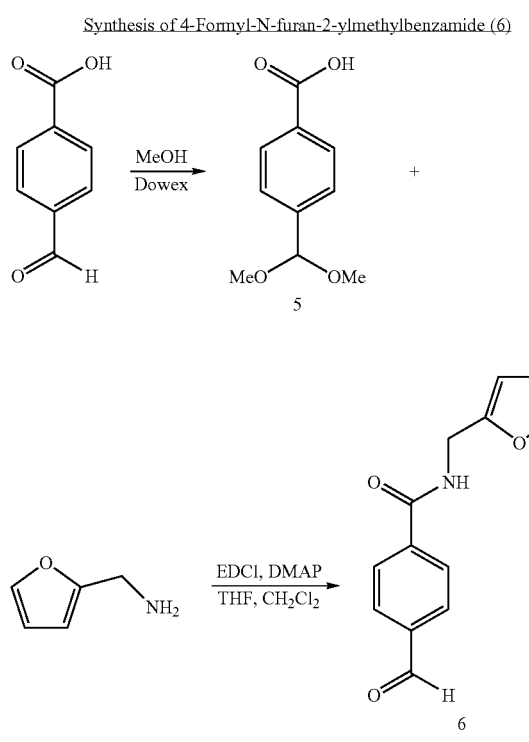

Step 1: 4-(Dimethoxymethyl)benzoic acid (5)

To a solution of 4-carboxybenzaldehyde (11.26 g, 75.0 mmol) in MeOH (200 mL) was added Dowex 50×8-100 ion exchange resin (2.25 g). The mixture was stirred at reflux for 16 hours. The resin was removed by vacuum filtration and the solvent was then removed by rotary evaporation. The white solid remaining was triturated with hot hexane, was filtered, and was dried in vacuo, yielding the title compound as a white powder (12.36 g, 84% yield). $^1$H NMR (400 MHz, CDCl$_3$): δ 8.03 (d, J=8.3 Hz, 2H), 7.54 (d, J=8.3 Hz, 2H), 5.45 (s, 1H), 3.34 (s, 6H).

Step 2: 4-Formyl-N-furan-2-ylmethylbenzamide (6)

A solution of 4-(dimethoxymethyl)benzoic acid 5 (2.94 g, 15 mmol), EDCI (5.75 g, 30 mmol), furfurylamine (3.5 mL, 37.5 mmol), and DMAP (122 mg, 1 mmol) in THF (200 mL) and CH$_2$Cl$_2$ (50 mL) was stirred at r.t. for 16 h. The solvent was removed by rotary evaporation and the resulting yellow oil was dissolved in CHCl$_3$ and was washed twice with 0.5 M HCl. The organic solution was then vigorously stirred with 1.0 M HCl for 2 h. The layers were separated and the organic phase was washed twice more with 1.0 M HCl and once with brine. The organic phase was dried over Na$_2$SO$_4$ and the solvent was removed by rotary evaporation. The crude product was crystallized from hot EtOAc, yielding the title compound as a pale yellow solid in 2 crops (2.09 g, 58% yield). $^1$H NMR (400 MHz, CDCl$_3$): δ 10.09 (s, 1H), 7.97 (s, 4H), 7.42 (m, 1H), 6.54 (br s, 1H), 6.39 (dd, J=2.0, 3.3 Hz, 1H), 6.35 (d, J=3.3 Hz, 1H), 4.69 (d, J=5.3 Hz, 2H).

Example 3

Synthesis of 4-Formyl-N-pyridin-3-ylmethyl-benzamide (8)

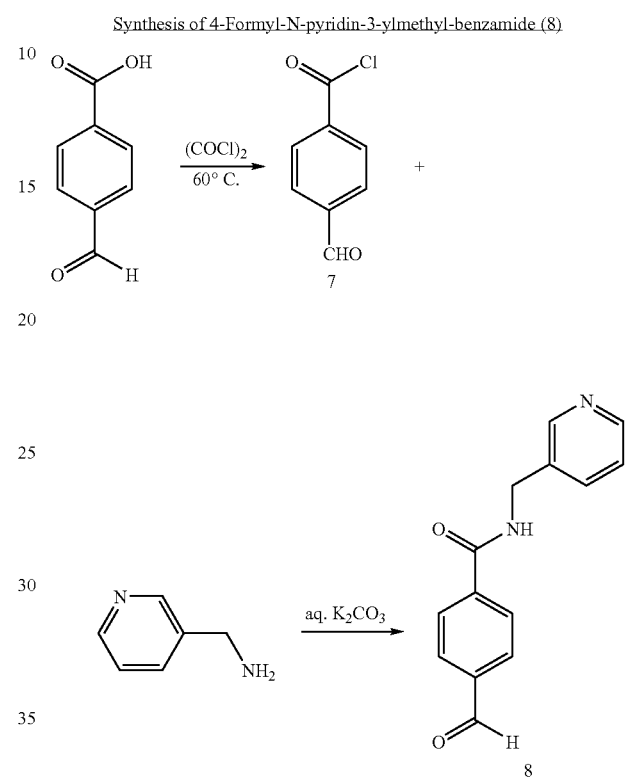

Step 1: 4-Formyl-benzoyl chloride (7)

To a solution of 4-carboxybenzaldehyde (4.50 g, 30 mmol) in CHCl$_3$ (6 mL) and DCM (5 mL), containing a catalytic amount of DMF, was added oxalyl chloride (7.7 mL, 90 mmol). The mixture was stirred at 50° C. for 3 hours. The reaction was concentrated in vacuo and the residue was dried.

Step 2: 4-Formyl-N-pyridin-3-ylmethyl-benzamide (8)

The compound obtained in the previous reaction was added to 2M aq. K$_2$CO$_3$ (50 mL, 100 mmol), followed by addition of 3-aminomethylpyridine (2.529 mL, 25 mmol). The vigorous reaction resulted in gas evolution and the formation of a precipitate. The reaction mixture was extracted with CHCl$_3$, and the product was purified by silica gel column chromatography (DCM-10% MeOH-MeOH). The compound was obtained in 578.9 mg yield and was characterized by NMR and LC/MS. $^1$H NMR (400 MHz, CD$_3$COCD$_3$): δ 4.67 (d, 2H), 7.33 (m, 1H), 7.80 (m, 1H), 8.02 (d, 2H), 8.13 (d, 2H), 8.48 (m, 1H), 8.56 (bs, 1H), 8.64 (m, 1H), 10.13 (s, 1H).

Example 4

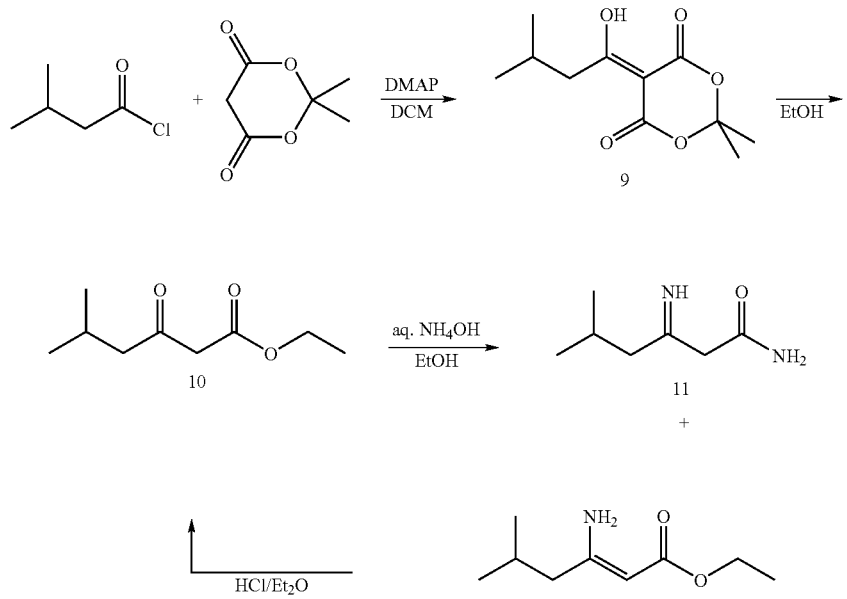

Step 1: 2,2-Dimethyl-5-(3-methyl-butyryl)-[1,3]dioxane-4,6-dione (9)

3-Methyl-butyryl chloride (7.40 mL, 60 mmol) was mixed at 0° C. with Meldrum's acid (2,2-dimethyl-1,3-dioxane-4,6-dione; 8.7 g, 60 mmol), and 4-dimethylaminopyridine (DMAP, 15.1 g, 124 mmol) in DCM. The reaction mixture was allowed to reach r.t. over 1.75 hr. and completion of the reaction was verified by TLC. The reaction mixture was diluted with DCM, was washed 3× with 5% aq. solution of potassium bisulfate and brine. The organic phase was than dried with MgSO$_4$. Crude product 9, 13.36 g) obtained after evaporation was used for next reaction without purification. $^1$H NMR (500 MHz, CDCl$_3$): δ 1.02 (d, 6H), 1.74 (s, 6H), 2.21 (hp, 1H), 2.99 (d, 2H).

Step 2: 5-Methyl-3-oxo-hexanoic acid ethyl ester (10)

Compound 9 was dissolved in EtOH (150 mL) and refluxed overnight. The reaction mixture was evaporated to yield product (10.315 g), which was shown by NMR to be pure. $^1$H NMR (500 MHz, CDCl$_3$): δ 0.93 (d, 6H), 1.28 (t, 3H), 2.16 (m, 1H), 2.42 (d, 2H), 3.41 (2, 2H), 4.20 (q, 2H).

Step 3: 3-Imino-5-methyl-hexanoic acid amide (11)

Compound 10 (1.85 g, 10.8 mmol) was dissolved in EtOH (5 mL) and 30% aq. ammonium hydroxide (5 mL, 88 mmol) was added. The reaction was stirred at r.t. overnight and the residue obtained after evaporation was purified by silica gel chromatography (0-6% MeOH/DCM). The target product was obtained in 23% yield (345 mg), in addition to amino crotonate (1.4 g). This latter material was hydrolyzed in Et$_2$O (100 mL)/1N HCl (20 mL) for 3 hrs, which recovered the starting material, which was then subjected again to ammonium hydroxide treatment, to yield an additional 230 mg of target product. Structure and purity were confirmed by NMR.

$^1$H NMR (500 MHz, CDCl$_3$): δ 0.94 (d, 6H), 2.16 (m, 1H), 2.42 (d, 2H), 3.40 (d, 2H), 5.61 (bs, 1H), 7.02 (bs, 2H).

(Z)-3-Amino-pent-2-enoic acid amide and (Z)-3-amino-hex-2-enoic acid amide were synthesized by essentially the same methods, starting from 3-oxo-pentanoic acid ethyl ester and 3-oxo-hexanoic acid ethyl ester, respectively.

Example 5

Examples of dihydropyridine and pyridine formation

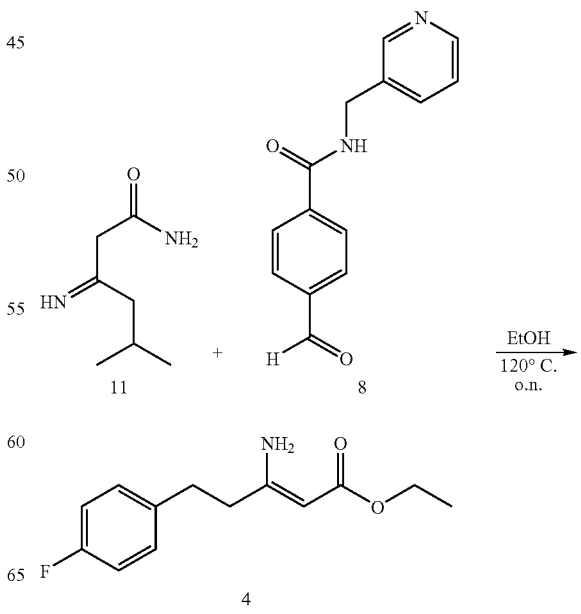

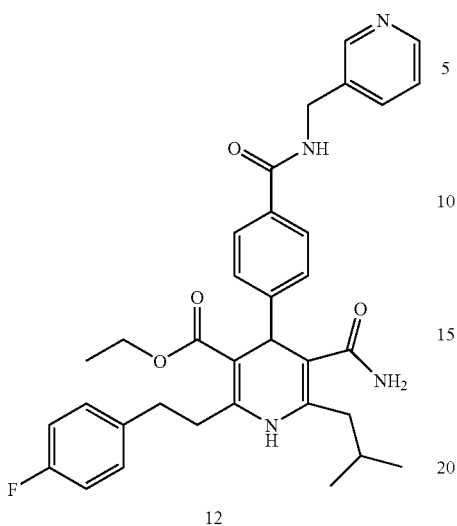

12

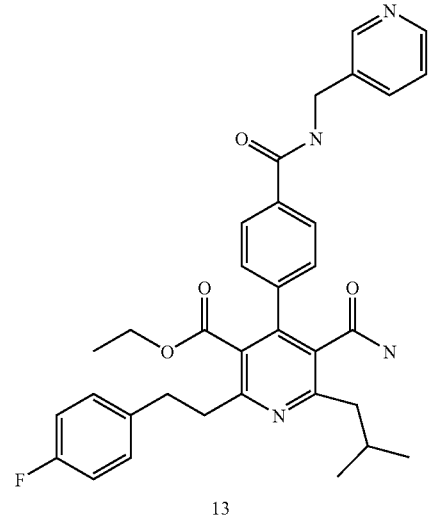

13

Step 1: 5-Carbamoyl-2-[2-(4-fluoro-phenyl)-ethyl]-6-isobutyl-4-{4-[(pyridin-3-ylmethyl)-carbamoyl]-phenyl}-1,4-dihydro-pyridine-3-carboxylic acid ethyl ester (12)

Ethyl 3-amino-5-(4-fluorophenyl)-2-pentenoate 4 (119 mg, 0.5 mmol), 4-formyl-N-pyridin-3-ylmethyl-benzamide 8 (120 mg, 0.5 mmol) and 3-Imino-5-methyl-hexanoic acid amide 11 (92 mg, 0.65 mmol) were dissolved in EtOH (4 mL). The reaction was stirred at 120° C. overnight. The crude reaction mixture was purified via reverse phase LC/MS to yield, 29 mg of target material. The compound was characterized by NMR and LC/MS. $^1$H NMR (500 MHz, CDCl$_3$): δ 8.79 (s, 1H), 8.51 (d, J=4.7 Hz, 1H), 8.29 (d, J=7.9 Hz, 1H), 7.68 (m, 4H), 7.28 (d, J=8.5 Hz, 1H), 7.08 (m, 2H), 6.90 (m, 2H), 4.63 (br. s, 2H), 4.04 (q, J=6.8 Hz, 2H), 3.37 (s, 1H), 2.86 (q, J=7.2 Hz, 2H), 2.78 (m, 3H), 2.50 (m, 1H), 1.65 (m, 1H), 1.17 (t, J=6.7 Hz, 3H), 0.82 (t, J=6.9 Hz, 6H).

Step 2: 5-Carbamoyl-2-[2-(4-fluoro-phenyl)-ethyl]-6-isobutyl-4-{4-[(pyridine-3-ylmethyl)-carbamoyl]-phenyl}-nicotinic acid ethyl ester (13)

An aqueous solution of CAN (1 M, 1 mL) was added to a solution of compound 12 (50 mg, 0.08 mmol) and trifluoroacetic acid (0.5 mL) in CHCl$_3$ (30 mL). The resulting mixture was vigorously stirred for 10 min at r.t. The organic layer was separated, washed with water, dried over Na$_2$SO$_4$, and concentrated in vacuo to yield the crude product. Purification by preparative LCMS (PE SCIEX, C$_{18}$, acetonitrile—water with 0.035% trifluoroacetic acid) yielded the title compound (2.6 mg, 95% purity by LCMS). $^1$H NMR (500 MHz, CDCl$_3$): δ 8.16 (s, 1H), 8.00 (br. d, 1H), 7.87 (m, 3H), 7.35 (m, 2H), 7.18 (d, J=8.5 Hz, 1H), 7.08 (m, 2H), 6.90 (m, 2H), 6.03 (br. s, 1H), 5.60 (br. s, 1H), 4.75 (m, 3H), 3.94 (q, J=7.0 Hz, 2H), 3.07 (m, 5H), 2.77 (d, J=7.6 Hz, 1H), 1.27 (m, 1H), 0.94 (m, 3H), 0.88 (t, J=7.4 Hz, 6H).

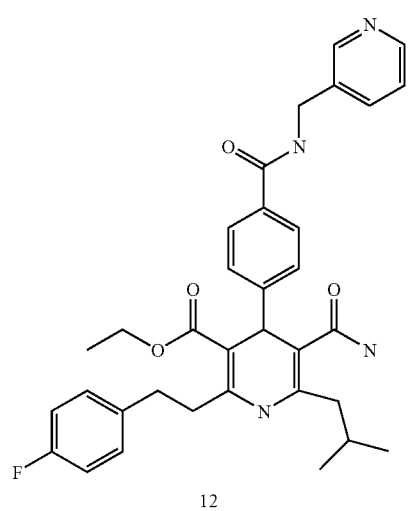

12

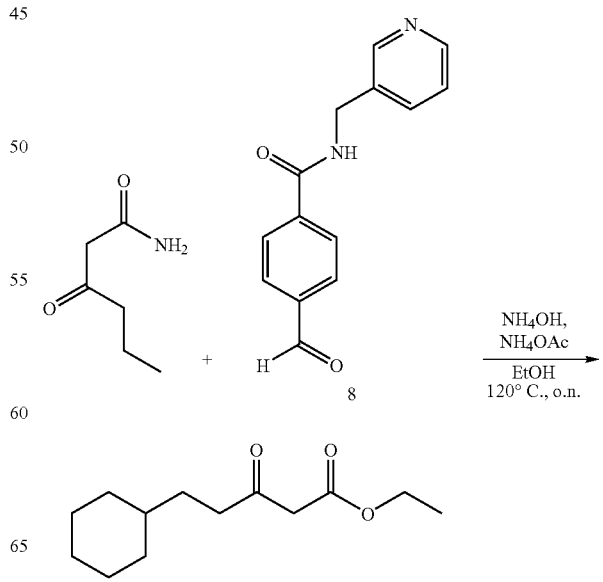

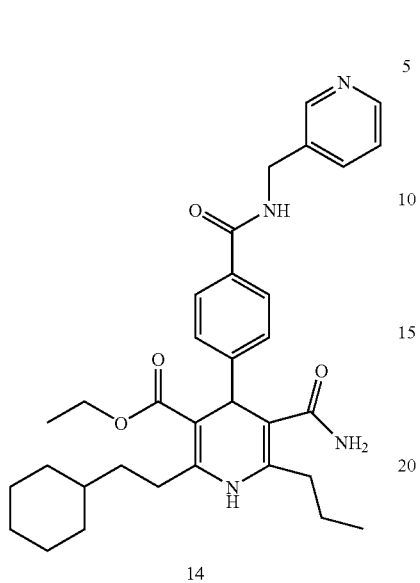

14

Step 1: 5-5-Carbamoyl-2-(2-cyclohexyl-ethyl)-6-propyl-4-{4-[(pyridin-3-ylmethyl)-carbamoyl]-phenyl}-1,4-dihydro-pyridine-3-carboxylic acid ethyl ester (14)

5-Cyclohexyl-3-oxo-pentanoic acid ethyl ester (339 mg, 1.5 mmol), 4-formyl-N-pyridin-3-ylmethyl-benzamide 8 (240 mg, 1.0 mmol) and 3-oxo-hexanoic acid amide (194 mg, 1.5 mmol) were dissolved in EtOH (2 mL). Amonium acetate (100 mg) and ammonium hydroxide (0.2 mL) were added and the reaction was stirred at 120° C. overnight. The crude reaction mixture was purified via reverse phase HPLC to yield the target material.

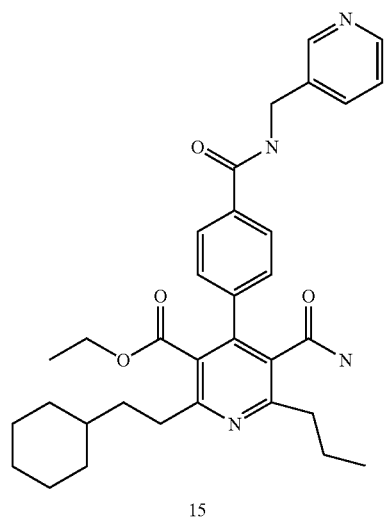

15

Step 2: 5-Carbamoyl-2-(2-cyclohexyl-ethyl)-6-propyl-4-{4-[(pyridin-3-ylmethyl)-carbamoyl]-phenyl}-nicotinic acid ethyl ester (15)

An aqueous solution of CAN (1 M, 1 mL) was added to a solution of compound 14 prepared as described above (~0.15 mmol) and trifluoroacetic acid (0.5 mL) in CHCl₃ (50 mL). The resulting mixture was vigorously stirred for 10 min at r.t. The organic layer was separated, washed with water, dried over Na₂SO₄, and concentrated in vacuo to yield the crude product. Purification by silica gel chromatography (0-10% MeOH/DCM) yielded the title compound (36 mg, 95% purity by LCMS). LC/MS (gradient 10-95% in 5 min.) R.T.=3.46 min. Calculated mass=556.3. Mass observed=556.8. $^1$H NMR (400 MHz, CDCl₃—CD₃OD): δ 0.93 (t, 3H), 0.98 (t, 3H), 1.10-1.26 (m, 5H), 1.35-1.40 (m, 2H), 1.53-1.80 (m, 8H), 2.79-2.84 (m, 4H), 3.95 (q, 2H), 4.65 (d, 2H), 7.38 (d, 2H), 7.62 (bs, 1H), 7.83 (d, 2H), 8.12 (d, 1H), 8.56 (bs, 1H), 8.68 (bs, 1H), 8.90 (t, 1H).

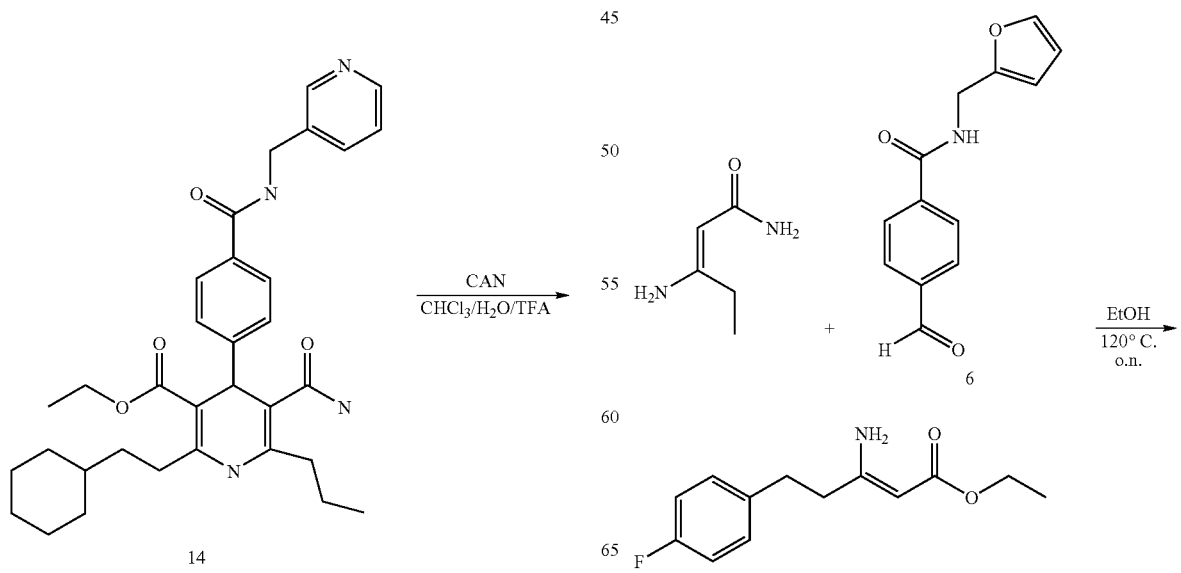

31

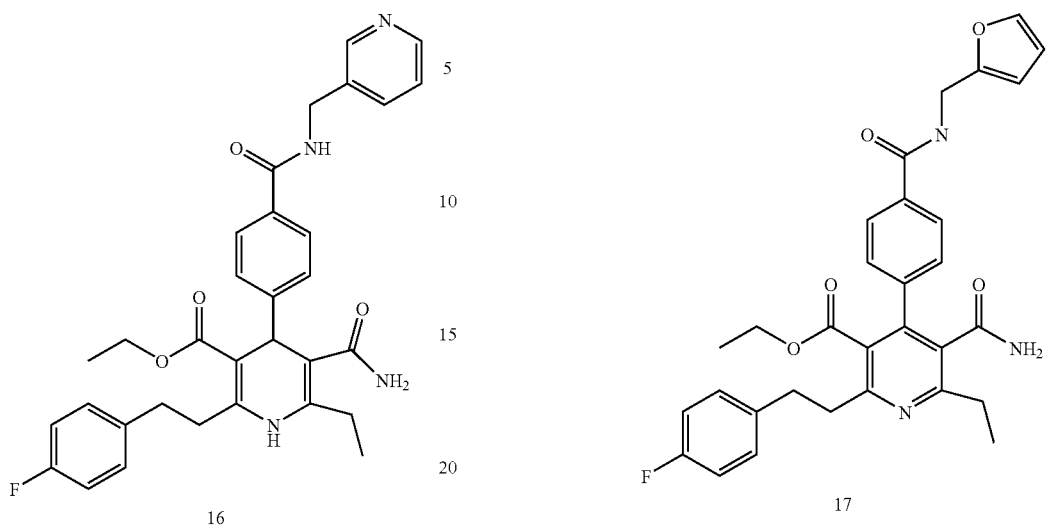

16

Step 1: 5-Carbamoyl-6-ethyl-2-[2-(4-fluoro-phenyl)-ethyl]-4-{4-[(pyridin-3-ylmethyl)-carbamoyl]-phenyl}-1,4-dihydro-pyridine-3-carboxylic acid ethyl ester (16)

Ethyl 3-amino-5-(4-fluorophenyl)-2-pentenoate 4 (115 mg, 0.49 mmol), 4-formyl-N-furan-2-ylmethyl-benzamide 6 (111 mg, 0.49 mmol) and (E)-3-amino-pent-2-enoic acid amide (70 mg, 0.60 mmol) were dissolved in EtOH (1.5 mL). The reaction was stirred at 120° C. overnight. The crude reaction mixture was diluted with 4 mL DCM and 2 mL of this solution was carried on into step 2 without further purification.

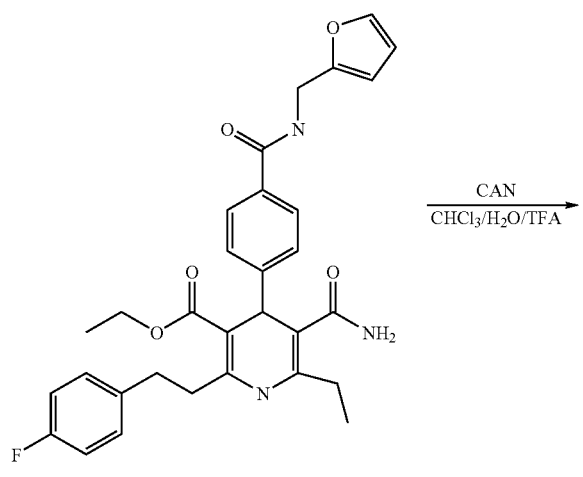

16

32

-continued

17

Step 2: 5-Carbamoyl-6-ethyl-2-[2-(4-fluoro-phenyl)-ethyl]-4-{4-[(furan-2-ylmethyl)-carbamoyl]-phenyl}-nicotinic acid ethyl ester (17)

An aqueous solution of CAN (1 M, 1 mL) was added to 2 mL of DCM solution of compound 16 (~0.25 mmol) and trifluoroacetic acid (0.1 mL). The resulting mixture was vigorously stirred for 20 min at r.t. The organic layer was separated, washed with water, dried over $MgSO_4$, and concentrated in vacuo to yield the crude product. Purification by preparative LCMS (PE SCIEX, $C_{18}$, acetonitrile—water with 0.035% trifluoroacetic acid) yielded the title compound in 18.5 mg yield. LC/MS (gradient 40-99%, 5 min.) RT=3.215. Calculated mass=243.2. Mass observed=243.7. $^1$H NMR (500 MHz, $CDCl_3$): δ 0.88 (t, 3H), 1.36 (t, 3H), 2.98 (bq, 2H), 3.07 (bq, 2H), 3.15 (bq, 2H), 3.94 (q, 2H), 4.65 (d, 2H), 5.61 (bs, 1H), 6.32 (m, 1H), 6.36 (m, 1H), 6.61 (bt, 1H), 6.96 (t, 2H), 7.18 (t, 2H), 7.39 (s, 1H), 7.40 (d, 2H), 7.81 (d, 2H).

Example 6

Binding Assay

Calcitonin binding assay. Competition binding assays are carried out using the T47D cell line (American Type Culture Collection (catalog #HTB-133). T47D cells are a human breast cancer cell line that expresses functional calcitonin receptors. Cells are plated at $5 \times 10^4$ cells/well in 96-well plates and are cultured overnight at 37° C. in 5% $CO_2$. Culture media is aspirated, the cells are washed in serum-free culture medium containing 0.1% (w/v) bovine serum albumin, and are incubated with $^{125}$I-labeled salmon calcitonin (100,000 cpm; 80-120 pmol/liter; Amersham Biosciences, Piscataway, N.J.) and appropriate concentrations of test or reference compounds. Non-specific binding of $^{125}$I-labeled calcitonin is assessed using 300 nM unlabelled salmon calcitonin. After incubation for 1 hr at 37° C. the medium is aspirated and the cells are washed with 4° C. phosphate-buffered saline. Cells and bound radioactivity are recovered from the wells using 0.5 M NaOH and are counted using a Packard automatic γ-scintillation spectrometer.

Example 7 cAMP Activity Assays

In T47D cells: Calcitonin cAMP activity assay. The functional assay for calcitonin agonists is carried out with intact T47D cells (American Type Culture Collection (catalog #HTB-133) using accumulation of cAMP as a readout. T47D cells are plated at $5\times10^3$ cells/well in 96-well plates and are cultured overnight at 37° C. in 5% $CO_2$. Culture media is aspirated and is replaced with 50 μL/well of serum-free culture medium containing 20 mM HEPES (pH 7.4) and 0.1% (w/v) bovine serum albumin (Assay Medium). After incubation for 10 min at 37° C., 50 μL of assay medium containing 1 mM isobutylmethylxanthine and appropriate concentrations of test or reference compounds is added. The cells are incubated for a further 30 min, the media is aspirated and the cells are lysed in 40 μL/well of phosphate-buffered saline containing 0.5% Triton X-100. The amount of cAMP in 10 μL of lysate is measured using a commercially available homogenous time-resolved fluorescent assay (CIS-US Inc., Bedford Mass.).

In HEK-293 cells: Amylin and calcitonin cAMP activity assay. This functional assay follows the general methodologies to assess the functional activities of the calcitonin receptor vs. the amylin receptor using transient expression techniques, as described in Christopoulos G, Perry K J, Morfis M, Tilakaratne N, Gao Y, Fraser N J, Main M J, Foord S M, Sexton P M., Mol Pharmacol. 1999 July; 56(1):235-42. (Multiple amylin receptors arise from receptor activity-modifying protein interaction with the calcitonin receptor gene product.)

Briefly, HEK-293 cells (American Type Culture Collection catalog #CRL-1573) are plated in T75 flasks at a density that will result in 50-60% confluency on Day 1. Recombinant human calcitonin receptor (CTR) can be cloned by RT-PCR from total RNA isolated from T47D cells. Recombinant rat calcitonin receptor (mCTR) can be cloned by RT-PCR from total rat brain RNA. Human RAMP3 can be cloned by PCR from a full-length IMAGE cDNA clone (catalog #EHS1001-42725) obtained from Open Biosystems. On Day 1, Fugene 6 (Roche Applied Science) is used according to the manufacturer's directions to transfect the cells with a total of 6 μg of plasmid DNA per flask, either 6 μg of an empty expression vector ('control'), 3 μg of human or rat CTR expression vector plus 3 μg of empty expression vector (the 'calcitonin receptor') or 3 μg of human or rat CTR expression vector plus 3 μg of human RAMP3 expression vector (the 'amylin receptor'). On Day 2, the transfected cells are replated in 96-well plates at a density of 10,000 cells/well in a total volume of 80-100 μL. On Day. 3, cAMP levels are quantitated as described above for the T47D cells, and compared to levels for calcitonin and/or amylin peptide.

Example 8

Compounds listed in the following Table were synthesized and assayed or will be assayed using the above procedures. Compound identity was verified by mass spectroscopy, with all molecules showing the expected mass ion. All compounds in the following Table exhibited activity in either the calcitonin or amylin cAMP functional assays or both or are expected to exhibit activity in one or both assays.

TABLE

| Compound No. | Structure | Name | Calc. MW |
|---|---|---|---|
| 13 | 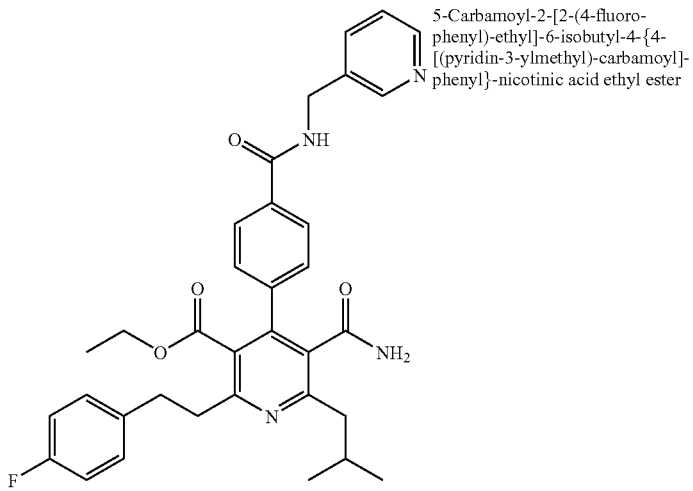 | 5-Carbamoyl-2-[2-(4-fluoro-phenyl)-ethyl]-6-isobutyl-4-{4-[(pyridin-3-ylmethyl)-carbamoyl]-phenyl}-nicotinic acid ethyl ester | 583 |

TABLE-continued

| Compound No. | Structure | Name | Calc. MW |
|---|---|---|---|
| 15 | 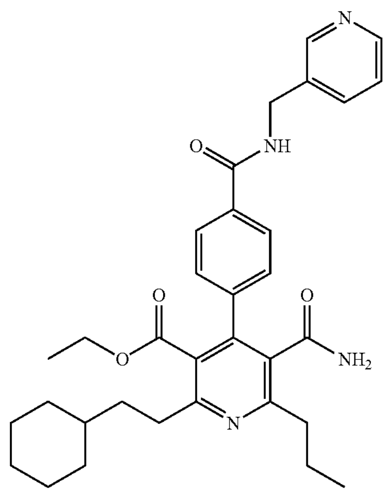 | 5-Carbamoyl-2-(2-cyclohexyl-ethyl)-6-propyl-4-{4-[(pyridin-3-ylmethyl)-carbamoyl]-phenyl}-nicotinic acid ethyl ester | 557 |
| 17 | 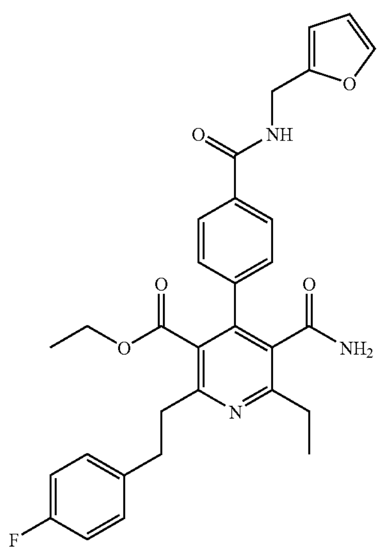 | 5-Carbamoyl-6-ethyl-2-[2-(4-fluoro-phenyl)-ethyl]-4-{4-[(furan-2-ylmethyl)-carbamoyl]-phenyl}-nicotinic acid ethyl ester | 544 |
| 18 | 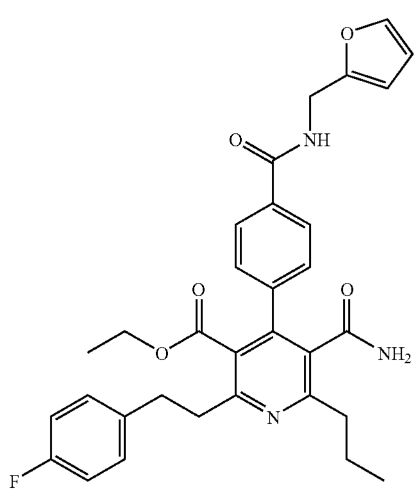 | 5-Carbamoyl-2-[2-(4-fluoro-phenyl)-ethyl]-4-{4-[(furan-2-ylmethyl)-carbamoyl]-phenyl}-6-propyl-nicotinic acid ethyl ester | 558 |

TABLE-continued

| Compound No. | Structure | Name | Calc. MW |
|---|---|---|---|
| 19 | 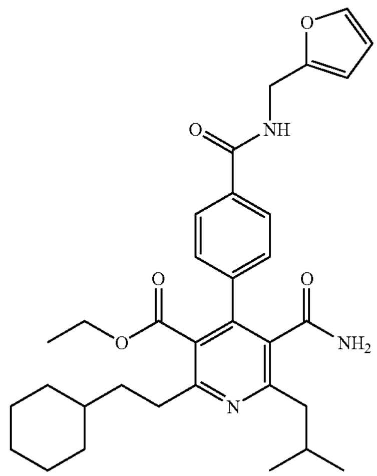 | 5-Carbamoyl-2-(2-cyclohexyl-ethyl)-4-{4-[(furan-2-ylmethyl)-carbamoyl]-phenyl}-6-isobutyl-nicotinic acid ethyl ester | 560 |
| 20 | 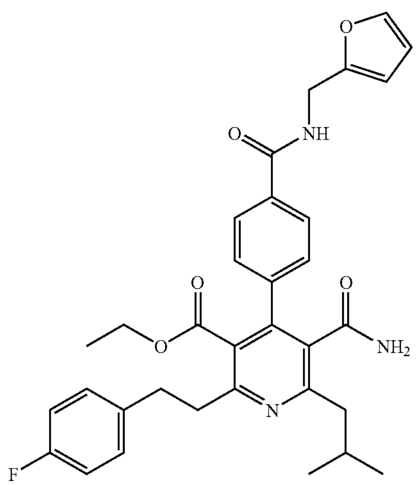 | 5-Carbamoyl-2-[2-(4-fluoro-phenyl)-ethyl]-4-{4-[(furan-2-ylmethyl)-carbamoyl]-phenyl}-6-isobutyl-nicotinic acid ethyl ester | 572 |
| 21 | 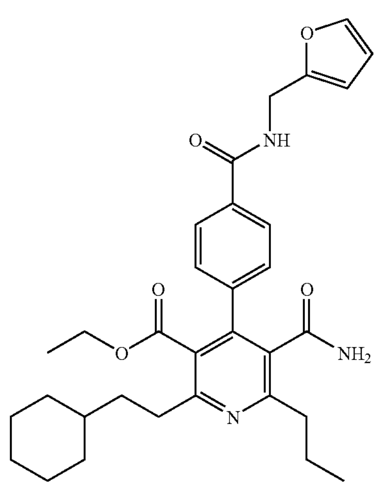 | 5-Carbamoyl-2-(2-cyclohexyl-ethyl)-4-{4-[(furan-2-ylmethyl)-carbamoyl]-phenyl}-6-propyl-nicotinic acid ethyl ester | 546 |

TABLE-continued

| Compound No. | Structure | Name | Calc. MW |
|---|---|---|---|
| 22 | 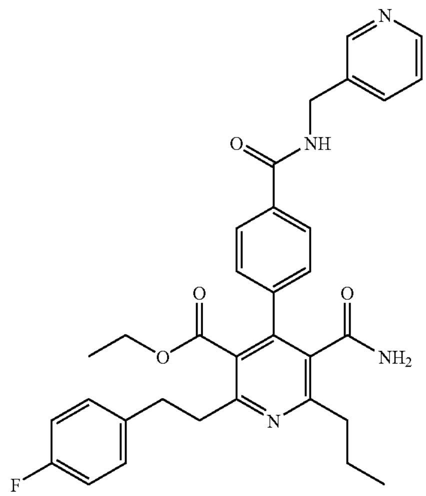 | 5-Carbamoyl-2-[2-(4-fluoro-phenyl)-ethyl]-6-propyl-4-{4-[(pyridin-3-ylmethyl)-carbamoyl]-phenyl}-nicotinic acid ethyl ester | 569 |
| 23 | 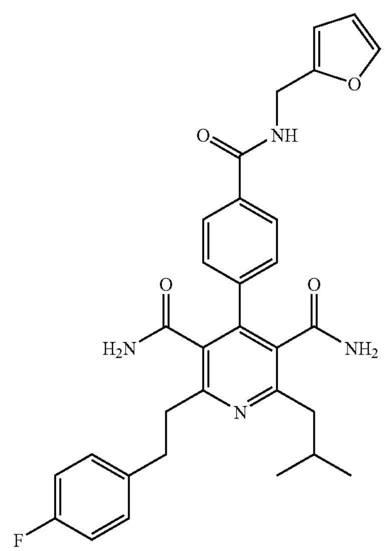 | 2-[2-(4-Fluoro-phenyl)-ethyl]-4-{4-[(furan-2-ylmethyl)-carbamoyl]-phenyl}-6-isobutyl-pyridine-3,5-dicarboxylic acid diamide | 543 |

While typical embodiments have been illustrated and described, it should be understood that changes and modifications can be made therein in accordance with ordinary skill in the art without departing from the invention in its broader aspects as defined in the following claims.

The invention claimed is:

1. A compound wherein the compound is
   5-Carbamoyl-2-[2-(4-fluoro-phenyl)-ethyl]-4-{4-[(furan-2-ylmethyl)-carbamoyl]-phenyl}-6-propyl-nicotinic acid ethyl ester;
   5-Carbamoyl-2-(2-cyclohexyl-ethyl)-4-{4-[(furan-2-ylmethyl)-carbamoyl]-phenyl}-6-isobutyl-nicotinic acid ethyl ester;
   5-Carbamoyl-2-[2-(4-fluoro-phenyl)-ethyl]-4-{4-[(furan-2-ylmethyl)-carbamoyl]-phenyl}-6-isobutyl-nicotinic acid ethyl ester;
   5-Carbamoyl-2-(2-cyclohexyl-ethyl)-4-{4-[(furan-2-ylmethyl)-carbamoyl]-phenyl}-6-propyl-nicotinic acid ethyl ester;
   5-Carbamoyl-2-[2-(4-fluoro-phenyl)-ethyl]-6-propyl-4-{4-[(pyridin-3-ylmethyl)-carbamoyl]-phenyl}-nicotinic acid ethyl ester;
   5-Carbamoyl-2-(2-cyclohexyl-ethyl)-6-propyl-4-{4-[(pyridin-3-ylmethyl)-carbamoyl]-phenyl}-nicotinic acid ethyl ester;
   2-[2-(4-Fluoro-phenyl)-ethyl]-4-{4-[(furan-2-ylmethyl)-carbamoyl]-phenyl}-6-isobutyl-pyridine-3,5-dicarboxylic acid diamide;
   5-Carbamoyl-6-ethyl-2-[2-(4-fluoro-phenyl)-ethyl]-4-{4-[(furan-2-ylmethyl)-carbamoyl]-phenyl}-nicotinic acid ethyl ester; or
   5-Carbamoyl-2-[2-(4-fluoro-phenyl)-ethyl]-6-isobutyl-4-{4-[(pyridin-3-ylmethyl)-carbamoyl]-phenyl}-nicotinic acid ethyl ester.

* * * * *